US012799520B2

(12) United States Patent
Valenta et al.

(10) Patent No.: US 12,799,520 B2
(45) Date of Patent: Nov. 17, 2026

(54) RADIOFREQUENCY IDENTIFICATION (RFID) BASED SYSTEM FOR STERILIZATION PROCESS MONITORING

(71) Applicants: O & M Halyard, Inc., Mechanicsville, VA (US); Georgia Tech Research Corporation, Atlanta, GA (US)

(72) Inventors: Christopher Valenta, Atlanta, GA (US); Jie Xu, Marietta, GA (US); Brian E. Lin, Cumming, GA (US); Anthony S. Spencer, Woodstock, GA (US); Marshall R. Dean, Cumming, GA (US); Ganesh B. Pavalarajan, Alpharetta, GA (US)

(73) Assignee: O&M Halyard, Inc., Glen Allen, VA (US)

( * ) Notice: Subject to any disclaimer, the term of this patent is extended or adjusted under 35 U.S.C. 154(b) by 403 days.

(21) Appl. No.: 18/477,988

(22) Filed: Sep. 29, 2023

(65) Prior Publication Data

US 2024/0110218 A1 Apr. 4, 2024

Related U.S. Application Data

(60) Provisional application No. 63/412,002, filed on Sep. 30, 2022.

(51) Int. Cl.
*C12Q 1/22* (2006.01)
*A61L 2/28* (2006.01)
(Continued)

(52) U.S. Cl.
CPC .................. *C12Q 1/22* (2013.01); *A61L 2/28* (2013.01); *G06K 7/10405* (2013.01); *G06K 19/0723* (2013.01); *A61L 2103/23* (2026.01)

(58) Field of Classification Search
USPC .......................................................... 324/525
See application file for complete search history.

(56) References Cited

U.S. PATENT DOCUMENTS 6,764,832 B2 7/2004 Restaino
8,127,593 B2 3/2012 Moularat
(Continued)

FOREIGN PATENT DOCUMENTS

CN 112 156 217 A 1/2021
EP 0 152 298 A2 8/1985
(Continued)

OTHER PUBLICATIONS

Busman et al., "Volatile Organic Compound Profile Fingerprints Using DART-MS Shows Species-Specific Patterns in *Fusarium* Mycotoxin Producing Fungi", Journal of Fungi, vol. 8. No. 1, Dec. 21, 2021, 18 pages.
(Continued)

*Primary Examiner* — Farhana A Hoque
(74) *Attorney, Agent, or Firm* — Dority & Manning, P.A.

(57) ABSTRACT

A biological indicator system for determining the efficacy of a sterilization process is provided. The system includes a radiofrequency identification sensing board having a radiofrequency identification tag, a microcontroller/digital electronics, a sensing pad, and a circuit coupled to the sensing pad that measures an impedance level or a resistance level of the sensing pad upon exposure to a volatile organic compound. The radiofrequency identification tag includes a radiofrequency integrated circuit and an antenna that communicates wirelessly with a radiofrequency identification reader to transmit data associated with the impedance or resistance levels measured from the sensing pad. The data can be transmitted in real-time during incubation, and this data can then be sent to a user interface to determine the efficacy of a sterilization process when the biological indi-
(Continued)

cator system is placed in a sterilization chamber during a sterilization cycle. A method of using the system is also provided.

35 Claims, 7 Drawing Sheets

(51) Int. Cl.
*A61L 103/00* (2026.01)
*G06K 7/10* (2006.01)
*G06K 19/07* (2006.01)

(56) References Cited

U.S. PATENT DOCUMENTS

| | | | |
|---|---|---|---|
| 8,318,452 B2 | 11/2012 | Rambach | |
| 8,410,562 B2 | 4/2013 | Lazarus et al. | |
| 8,736,000 B1 | 5/2014 | Manginell et al. | |
| 10,077,464 B2 | 9/2018 | Cellier et al. | |
| 10,876,144 B2 | 12/2020 | Centanni et al. | |
| 10,889,848 B2 | 1/2021 | Franciskovich et al. | |
| 10,900,062 B2 | 1/2021 | Franciskovich et al. | |
| 2003/0049718 A1 | 3/2003 | Restaino | |
| 2008/0145879 A1 | 6/2008 | Orenga et al. | |
| 2009/0280524 A1 | 11/2009 | Rambach | |
| 2011/0180884 A1 | 7/2011 | Lazarus et al. | |
| 2015/0329897 A1 | 11/2015 | Cellier et al. | |
| 2016/0178538 A1* | 6/2016 | Bommarito | G01N 22/04 324/634 |
| 2017/0252474 A1* | 9/2017 | Thompson | A61L 2/28 |
| 2018/0107909 A1 | 4/2018 | Swager et al. | |
| 2019/0106726 A1 | 4/2019 | Cregger et al. | |
| 2021/0311002 A1 | 10/2021 | Ahimou et al. | |

FOREIGN PATENT DOCUMENTS

| | | |
|---|---|---|
| EP | 0 433 053 A1 | 6/1991 |
| EP | 3 408 405 B1 | 6/2020 |
| WO | WO 2008/082728 A2 | 7/2008 |
| WO | WO 2008/125770 A1 | 10/2008 |
| WO | WO 2019/014313 A1 | 1/2019 |
| WO | WO 2019/014316 A1 | 1/2019 |
| WO | WO 2019/074639 A1 | 4/2019 |

OTHER PUBLICATIONS

Khalid et al., "A Survey of Battery-Less RFID-Based Wireless Sensors", Micromachines, vol. 12, No. 7, Jul. 12, 2021, 26 pages.

International Search Report and Written Opinion for PCT/US2023/034125, dated Jan. 31, 2024, 26 pages.

Albert et al., "Biological indicators for steam sterilization: characterization of a rapid biological indicator utilizing *Bacillus stearothermophilus* spore-associated alpha-glucosidase enzyme", Journal of Applied Microbiology, vol. 85, 1998 10 pages.

Altaee et al., "Characterization of Metabolites Produced by *E. Coli* and Analysis of Its Chemical Compounds Using GC-MS", International Journal of Current Pharmaceutical Review and Research, vol. 7, Dec. 2016, 7 pages.

Altaee et al., "Detection of Volatile Compounds Produced by *Pseudomonas aeruginosa* Isolated from UTI Patients by Gas Chromatography-Mass Spectrometry", International Journal of Current Pharmaceutical Review and Research, vol. 8, Dec. 2016, 9 pages.

Billington et al., "Isolation of the Putative Intermediate 4-Methylthio-2-Oxobutanoate from Culture Fluids of Bacteria and Fungi", Biochem. J., vol. 182, 1979, pp. 827-836.

Blake et al., "Immunomagnetic Detection of *Bacillus stearothermophilus* Spores in Food and Environmental Samples", Applied and Environmental Microbiology, vol. 63, No. 5,May 1997, pp. 1643-1646.

Boland et al., "Complete spore-cortex hydrolysis during germination of *Bacillus subtilis* 168 requires SleB and YpeB", Microbiology, vol. 146, 2000, pp. 57-64.

Bressuire-Isoard, et al., "Sporulation environment influences spore properties in *Bacillus*: evidence and insights on underlying molecular and physiological mechanism", FEMS Microbiology Revies, vol. 42, No. 5, 2018 pp. 614-626.

Cernosek et al., "Volatile Organic Compound Profiling from Postmortem Microbes using Gas Chromatography-Mass Spectrometry", Journal of Forensic Sciences, vol. 65. No. 1, Jan. 2020, 11 pages.

Chandrapati et al., "Inducible β-glucosidase synthesis during germination and outgrowth of *Bacillus subtilis* ATCC 9372 spores", Letters in Applied Microbiology, vol. 36, 2003, pp. 15-19.

Coleman et al., "How Moist Heat Kills Spores of *Bacillus subtilis*", Journal of Bacteriology, vol. 189, No. 23, Dec. 2007, pp. 8458-8466.

Cortezzo, et al., "Analysis of factors that influence the sensitivity of spores of *Bacillus subtilis* to DNA damaging chemicals", Journal of Applied Microbiology, vol. 98, 2005, pp. 606-617.

Cortezzo et al., "Treatment with oxidizing agents damages the inner membrane of spores of *Bacillus subtilis* and sensitizes spores to subsequent stress", Journal of Applied Microbiology, vol. 97, 2004, pp. 838-852.

Cowan et al., "Lipids in the inner membrane of dormant spores of *Bacillus* species are largely immobile". PNAS, vol. 101, No. 20, May 18, 2004, pp. 7733-7738.

Dadd et al., "Germination of spores of *Bacillus subtilis* var. *niger* following exposure to gaseous ethylene oxide", Journal of Applied Bacteriology, vol. 60, 1986, 5 pages.

Dills et al., "An Evaluation of Respiration Chain-Associated Functions During Initiation of Germination of *Bacillus megaterium* Spores", Biochimica et Biophysica Acta, vol. 541, 1978, pp. 301-311.

Elsden et al., "Volatile acid production from threonine, valine, leucine and isoleucine by clostridia", Archives of Microbiology, vol. 177, 1978, 1 page.

Francis et al., "Detecting Cortex Fragments During Bacterial Spore Germination", Journal of Visualized Experiments, Jun. 2016, 7 pages.

Fukushima et al., "A Polysaccharide Deacetylase Gene (*pdaA*) Is Required for Germination and for Production of Muramic δ-Lactam Residues in the Spore Cortex of *Bacillus subtilis*", Journal of Bacteriology, vol. 184, No. 21, Nov. 2002, pp. 6007-6015.

Gao et al., "Identification of endophytic Bacillus velezensis ZSY-1 strain and antifungal activity of its volatile compounds against *Alternaria solani* and *Botrytis cinerea*", Biological Control, vol. 105, 2017, pp. 27-39.

Goldman et al., "Pathways of Glucose Catabolismin *Bacillus cereus*", Journal of Bacteriology, vol. 87, No. 2, Feb. 1064, pp. 377-386.

Hachisuka, et al., "Studies on Spore Germination", Effect of Nitrogen Sources on Spore Germination, vol. 69, Sep. 24, 1954, pp. 399-406.

Hagen et al., "Survival of Microorganisms in a Simulated Martian Environment", Applied Microbiology, vol. 15, No. 2, Mar. 1967, pp. 285-291.

Hills, G.M., "Chemical Factors in the Germination of Spore-bearing Aerobes. The Effects of Amino-acids on the Germination of *Bacillus anthracis*, with some Observations on the Relation of Optical Form to Biological Activity", Microbiological Research Department, vol. 45, 1950, 8 pages.

Huesca-Espitia et al., "Effects of steam autoclave treatment on *Geobacillus stearothermophilus* spores", Journal of Applied Microbiology, vol. 121, 2016, pp. 1300-1311.

Kanda et al., "Germination-initiating Activities for *Bacillus subtilis* Spores of Analogues of $_L$-Alanine Derived by Modification a the Amino or Carboxyl Group", Journal of General Microbiology, vol. 134, 1988, pp. 2747-2755.

Korza et al., "Levels of L-malate and other low molecular weight metabolites in spores of *Bacillus* species and *Clostridium difficle*", PLOS ONE, Aug. 29, 2017, 11 pages.

Leggett et al., "Bacterial spore structures and their protective role in biocide resistance", Journal of Applied Microbiology, vol. 113, 2012, pp. 485-498.

Magge et al., "Role of Dipicolinic Acid in the Germination, Stability and Viability of Spores of *Bacillus subtilis*", Journal of Bacteriology, vol. 190, No. 14, Jul. 2008, pp. 4798-4807.

(56) References Cited

OTHER PUBLICATIONS

Maruyama et al., "Glucose Catabolismuring Germination of *Bacillus megaterium* Spores", Journal of Bacteriology, vol. 141, No. 3, Mar. 1980, pp. 1443-1446.
Mckenney et al., "The *Bacillus subtilis* endospore: assembly and functions of the multilayered coat", Nature Review, Microbiology, vol. 11, Jan. 2013, 13 pages.
Melly et al., "Studies on the mechanism of killing of *Bacillus subtilis* spores by hydrogen peroxide", Journal of Applied Microbiology, vol. 93, 2002, pp. 316-325.
Moir et al., "Spore Germination", American Society for Microbiology, 2016, 20 pages.
Nitta et al., "$_L$-Amino Acid Dehydrogenases in *Bacillus subtilis* Spores", Journal of Bacteriology, vol. 117, No. 2, Feb. 1974, pp. 588-592.
Orlowski et al., "Inactivation of Glucose 6-Phosphate Dehydrogenase during Germination and Outgrowth of *Bacillus cereus* T Endospores", Biochem. J., vol. 148, 1975, pp. 259-268.
Paidhungat et al., "Spore Germination and Outgrowth", Sep. 13, 2001, 13 pages.
Popham et al., "Muramic lactam in peptidoglycan of *Bacillus subtilis* spores is required for spore growth but not for spore dehydration or heat resistance". Proc. Natl. Acad. Sci. USA, vol. 93, Dec. 1996, p. 15405-15410.
Popham, D.L., "Specialized peptidoglycan of the bacterial endospore: the inner wall of the lockbox", CMLS Cellular and Molecular Life Sciences, vol. 59, 2002, pp. 426-433.
Popham et al., "Spore Peptidoglycan", Microbiology Spectrum, American Society for Microbiology Press, Dec. 18, 2015, 21 pages.
Prasad, Chandon, "Initiation of Spore Germination in *Bacillus subtilis*: Relationship to Inhibition of $_L$-Alaine Metabolism", Journal of Bacteriology, vol. 119, No. 3, Sep. 1974, pp. 805-810.
Prasad et al., "Initiation of Spore Germination in Glycolytic Mutants of *Bacillus subtilis*", Journal of Bacteriology, vol. 110, No. 1, Apr. 1972, pp. 321-328.
Robinson et al., "Solid-state fermentation: a promising microbial technology for secondary metabolite production", Appl., Microbiol. Biotechbol., vol. 55, 2001, pp. 284-289.
Russell, A.D., "Bacterial Spores and Chemical Sporicidal Agents", Clinical Microbiology Reviews, vol. 3, No. 2, Apr. 1990, pp. 99-119.
Rutala et al., "Guideline for Disinfection and Sterilization in Healthcare Facilities, 2008", https://www.cdc.gov/infectioncontrol/pdf/guidelines/disinfection-guidelines-H.pdf.
Ryu et al., "Bacterial Volatile Compounds as Mediators of Airborne Interactions", https://doi.org/10.1007/978-981-15-7293-7_1.
Sangavai C., "Amino acid catabolism-directed biofuel production in *Clostridium sticklandii*: An insight into model-driven systems engineering", Biotechnology Reports, vol. 16, 2017, pp. 32-43.
Santo et al., "Ultrastructural Analysis During Germination and Outgrowth of *Bacillus subtilis* Spores", Journal of Bacteriology, vol. 120, No. 1, Oct. 1974, pp. 475-481.
Sella et al., "Life cycle and spore resistance of spore-forming *Bacillus astrophaeus*", Microbiological Research, vol. 169, 2014, pp. 931-939.
Setlow et al., "Analysis of a-glucosidase enzyme activity used in a rapid test for steam steri I ization assurance", Journal of Applied Microbiology, vol. 120, 2016, pp. 1326-1335.
Setlow et al., "Analysis of the germination kinetics of individual *Bacillus subtilis* spores treated with hydrogen peroxide or sodium hypochlorite", Letters in Applied Microbiology, vol. 57, 2013, pp. 259-265.
Setlow et al., "Biochemical Studies of Bacterial Sporulation and Germination", The Journal of Biological Chemistry, vol. 245, No. 14, 1970, 8 pages.
Setlow et al., "Germination of Spores of the Orders *Bacillales* and *Clostridiales*", Annual Review of Microbiology, vol. 71, 2017, 22 pages.
Setlow et al., "Levels of Oxidized and Reduced Pyridine Nucleotides in Dormant Spores and During Growth, Sporulation, and Spore Germination of *Bacillus megaterium*", Journal of Bacteriology, vol. 129, No. 2, Feb. 1977, pp. 857-865.
Setlow et al., "Protein Metabolism during Germination of *Bacillus megaterium* Spores", The Journal of Biological Chemistry, vol. 250, No. 2, 1975, pp. 623-630.
Setlow, Peter, "Small, Acid-Soluble Spore Proteins of *Bacillus* Species: Structure, Synthesis, Genetics, Function and Degradation", Annual Review Microbiol., vol. 42, 1988, 20 pages.
Setlow, P., "Spores of *Bacillus subtilis*: their resistance to and killing by radiation, heat and chemicals", Journal of Applied Microbiology, vol. 101, 2006, pp. 514-525.
Sinai et al., "The Molecular Timeline of a Reviving Bacterial Spore", Molecular Cell, vol. 57, Feb. 19, 2015, pp. 695-707.
Stöver et al., "Regulation of Synthesis of the *Bacillus subtilis* Transition-Phase, Spore-Associated Antibacterial Protein TasA", Journal of Bacteriology, vol. 181, No. 17, Oct. 1999, pp. 5476-5481.
Tehri et al., "Biomarkers of bacterial spore germination", Annals of Microbiology, vol. 68, 2018, pp. 513-523.
Waller et al., "Ruthenium red staining for ultrastructural visualization of a glycoprotein layer surrounding the spore of *Bacillus anthracis* and *Bacillus subtilis*", Journal of Microbiological Methods, vol. 58, 2004, pp. 23-30.
Wang et al., "Kinetics of Germination of Wet-Heat-Treated Individual Spores of *Bacillus* Species, Monitored by Raman Spectroscopy and Differential Interference Contrast Microscopy", Applied and Environmental Microbiology, vol. 77, No. 10,m May 2011, pp. 3368-3379.
Wilson et al., "Bio-production of gaseous alkenes: ethylene, isoprene, isobutene", Biotechnology for Biofuels, vol. 11, 2018, 11 pages.
Yu et al., "Identification of volatile compounds released by myxobacteria *Sorangium cellulosum* ABH103-1", African Journal of Microbiology Research, vol. 5, Feb. 11, 2011, pp. 353-358.
Abdulhadi et al., "Multiport UHF RFID-Tag Antenna for Enhanced Energy Harvesting of Self- Powered Wireless Sensors", IEEE Transactions on Industrial Informatics, vol. 12, No. 2, Apr. 2016, 8 pages.

* cited by examiner

RADIOFREQUENCY IDENTIFICATION (RFID) BASED SYSTEM FOR STERILIZATION PROCESS MONITORING

RELATED APPLICATIONS

The present application claims priority to U.S. Provisional Patent Application No. 63/412,002, having a filing date of Sep. 30, 2022, the entire contents of which are incorporated herein by reference.

FIELD OF THE INVENTION

The present invention relates generally to a system used to verify the effectiveness of a sterilization process.

BACKGROUND

Sterilization is a process to produce a product that is free from viable microorganisms (e.g., *Geobacillus* or *Bacillus* species). The sterilization process must be routinely monitored to assure the safety of any product to be sterilized (e.g., medical devices, instruments, etc.) post-sterilization. Common sterilization monitors include physical, chemical, and biological indicators. Physical indicators monitor the time, temperature, and pressure of the sterilization process to ensure the physical environment was conducive for a successful sterilization process. A chemical indicator is a non-biological indicator test system that reveals a change in one or more pre-defined process variables based on a chemical or physical change resulting from exposure to a process. Biological indicators (BIs) are process-monitoring devices containing a known population of highly resistant spores that can measure the effectiveness of a sterilization process. Compared to physical and chemical-based indicators, BIs tend to provide a more accurate assessment of a successful or failed sterilization process. However, the response time for determining whether a sterilization process was successful or failed using BIs requires prolonged incubation to confirmation the presence or absence of bacterial growth, where the presence of bacterial growth indicates a failed sterilization process, and the absence of bacterial growth indicates a successful sterilization process. For instance, depending on the manufacturer and the technology utilized, the time for BI incubation can be 48 hours or longer. Therefore, there is a need for a biological indicator system that can provide near real time or process time biological indicator results during incubation to ensure the safety and efficacy of the various sterilization processes (e.g., steam, vaporized hydrogen peroxide, and ethylene oxide (EtO)).

SUMMARY OF THE INVENTION

Objects and advantages of the invention will be set forth in part in the following description, or may be obvious from the description, or may be learned through practice of the invention.

In one embodiment of the present invention, a biological indicator system for determining the efficacy of a sterilization process is provided. The biological indicator system can include a radiofrequency identification sensing board comprising a radiofrequency identification tag that includes a radiofrequency integrated circuit and an antenna, a microcontroller/digital electronics, a sensing pad, and a circuit coupled to the sensing pad and configured to measure an impedance level or resistance level of the sensing pad upon exposure to a volatile organic compound. For instance, the circuit can include a resistivity circuit coupled to the sensing pad and configured to measure a resistance level of the sensing pad upon exposure to a volatile organic compound.

In another embodiment, the biological indicator system can further include a biological indicator and a growth medium, and the radiofrequency identification sensing board, the biological indicator, and the growth medium can be sealed within a container by a cap.

Further, a headspace distance between the growth medium and the cap can range from about 4 millimeters to about 16 millimeters. In addition, a filter can be disposed between the radiofrequency identification sensing board and the growth medium. Additionally, the filter can include a polymer coating having a thickness ranging from about 0.01 micrometers to about 5 micrometers.

In still another embodiment, the sensing pad can be disposed on a lower surface of the radiofrequency identification sensing board. Moreover, the sensing pad can be in contact with a gap electrode or an interdigitated electrode coated with a film. Further, the gap electrode can define a gap ranging from about 0.01 millimeters to about 0.3 millimeters. Additionally, the film can include a polymer and metal nanoparticles.

In yet another embodiment, the biological indicator system can include an array of sensing pads.

In one more embodiment, the biological indicator system can include an array of radiofrequency indicator tags.

In an additional embodiment, the biological indicator system can include a radiofrequency identification reader coupled to a user interface. Further, the radiofrequency identification reader can provide power to the radiofrequency identification sensing board. Likewise, the radiofrequency tag can transmit data to the radiofrequency identification reader at a frequency ranging from about 300 Megahertz to about 3 Gigahertz and/or at a frequency ranging from about 3 Megahertz to about 30 Megahertz.

In another embodiment, the radiofrequency identification sensing board can be free of a battery.

In still another embodiment, the biological indicator system can include a temperature sensor.

In another embodiment of the present invention, a method for determining the efficacy of a sterilization process via a biological indicator system including a radiofrequency identification sensing board, and a radiofrequency identification (RFID) reader is provided. The method includes exposing a sensing pad of the radiofrequency identification sensing board to vapor from headspace in a container, wherein the container includes a growth medium and a biological indicator; measuring an impedance level or a resistance level of the sensing pad; and sending data associated with the impedance level or the resistance level to a radiofrequency identification tag, wherein the presence of a volatile organic compound is determined if the impedance level or the resistance level is higher than a predetermined baseline impedance level or a predetermined baseline resistance level of the sensing pad, wherein the presence of the volatile organic compound indicates failure of the sterilization process.

In one embodiment, the method can further include transmitting the data to a radiofrequency identification reader.

In still another embodiment, the method can include sending the data from the radiofrequency identification reader to a user interface.

In yet another embodiment, the method can include measuring a temperature within the container via a temperature sensor.

In one more embodiment, the radiofrequency identification sensing board can include a radiofrequency tag that includes a radiofrequency integrated circuit and an antenna, a microcontroller, and a circuit configured to measure an impedance level or a resistance level of the sensing pad. Further, the RFID sensing board can include an array of radiofrequency indicator tags.

Additionally, in some embodiments, the radiofrequency tag can transmit data to the radiofrequency identification reader at a frequency ranging from about 300 Megahertz to about 3 Gigahertz and/or at a frequency ranging from about 3 Megahertz to about 30 Megahertz.

In another embodiment, the cap can seal the radiofrequency identification sensing board, the biological indicator, and the growth medium within the container, wherein a headspace distance between the growth medium and the radiofrequency identification sensing board can from about 4 millimeters to about 16 millimeters.

In an additional embodiment, a filter can be disposed between the radiofrequency identification sensing board and the growth medium. Further, the filter can include a polymer coating having a thickness ranging from about 0.1 micrometers to about 5 micrometers.

In still another embodiment, the sensing pad can be in contact with a gap electrode or an interdigitated electrode coated with a film comprising a polymer and metal nanoparticles. In addition, the gap electrode can define a gap ranging from about 0.01 millimeters to about 0.3 millimeters.

In one more embodiment, the RFID sensing board can include an array of sensing pads.

Further, the radiofrequency identification reader can be coupled to a user interface.

In yet another embodiment, the radiofrequency identification reader can provide power to the radiofrequency identification sensing board.

In another embodiment, the radiofrequency identification sensing board can be free of a battery.

Further, the sterilization process can utilize steam, hydrogen peroxide, or ethylene oxide.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
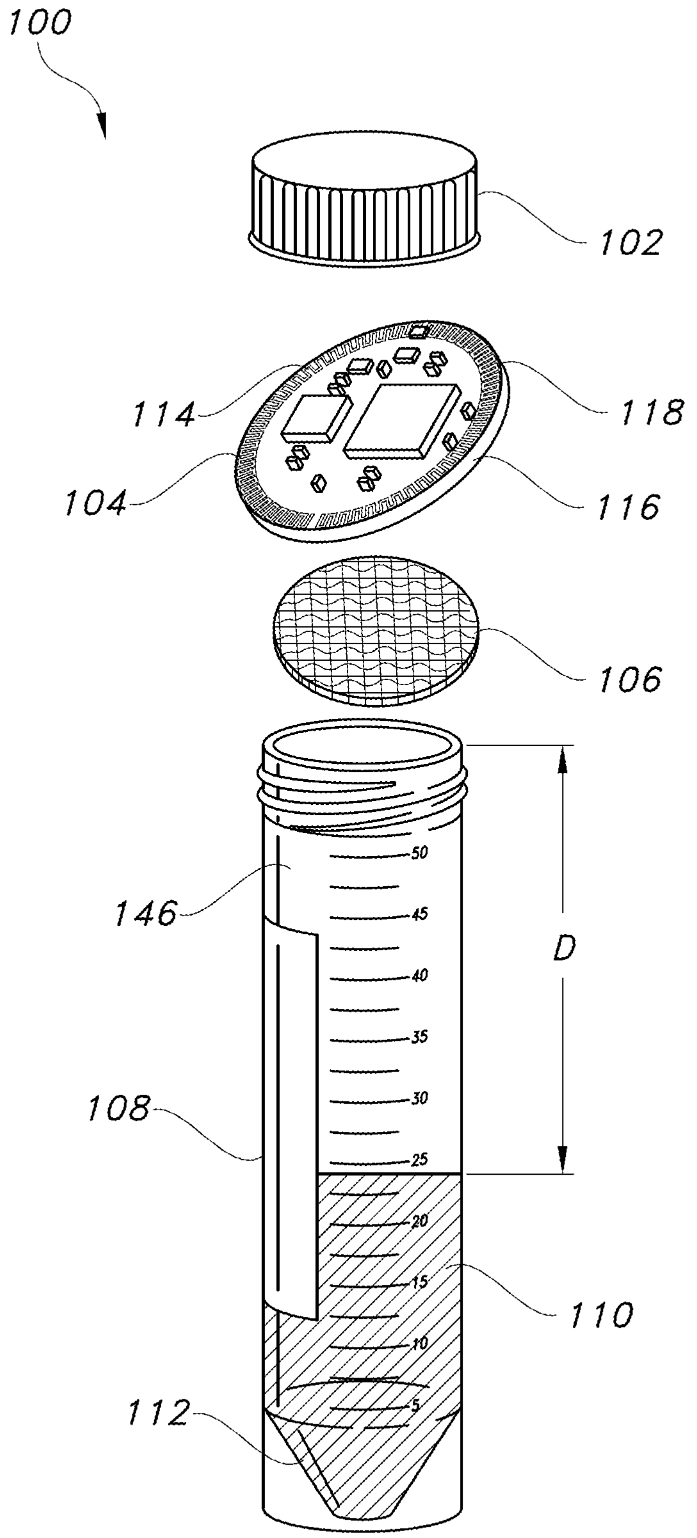
FIG. 1 is an exploded view of an embodiment of a biological indicator system contemplated by the present invention, including an RFID sensing board.

Reference will now be made in detail to one or more embodiments of the invention, examples of the invention, examples of which are illustrated in the drawings. Each example and embodiment is provided by way of explanation of the invention and is not meant as a limitation of the invention. For example, features illustrated or described as part of one embodiment may be used with another embodiment to yield still a further embodiment. It is intended that the invention include these and other modifications and variations as coming within the scope and spirit of the invention.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a biological indicator system for determining the efficacy of a sterilization process. The biological indicator system includes an integrated self-contained biological indicator (SCBI) including a radiofrequency identification sensing board. The radiofrequency identification sensing board includes a passive radiofrequency identification tag, a microcontroller, a sensing pad, and a circuit coupled to the sensing pad that measures an electrical property level (e.g., resistance, capacitance, and/or impedance level) of the sensing pad upon exposure to volatile organic compounds. The radiofrequency identification tag includes a radiofrequency integrated circuit and an antenna that communicates wirelessly with a radiofrequency identification reader to transmit data associated with the impedance levels or resistance levels measured from the sensing pad. The integrated SCBI is a self-contained and battery-free biological indicator presented in such a way that the primary package, intended for incubation, contains the incubation medium required for recovery of the test organism and a radiofrequency identification sensing board. The data can be transmitted in real-time when the biological indicator system sits in an incubator/autoreader, and this data can then be sent to a user interface to determine the efficacy of a sterilization process when the biological indicator system is placed in a sterilization chamber after a sterilization cycle. As such, manual steps for tracking and reporting of sterilization cycle results can be eliminated, which can help improve efficiency and accuracy when determining if a sterilization cycle was effective.

The present invention is also directed to a method for determining the efficacy of a sterilization process via a biological indicator system that includes an integrated SCBI. The integrated SCBI is a self-contained biological indicator presented in such a way that the primary package, intended for incubation, contains the incubation medium required for recovery of the test organism and radiofrequency identification sensing board and a radiofrequency identification reader. The method includes exposing a sensing pad of the radiofrequency identification sensing board to vapor from headspace in a container that includes a growth medium and a biological indicator; measuring an impedance level or a resistance level of the sensing pad; sending data associated with the impedance level or the resistance level to a radiofrequency identification tag; and transmitting the data to a radiofrequency identification reader. Further, the presence of volatile organic compounds is determined if the impedance level or the resistance level is higher than a predetermined baseline impedance level or a predetermined baseline resistance level of the sensing pad, and the presence of the volatile organic compounds indicates failure of the sterilization process.

The present inventors have found that the biological indicator systems and methods of the present invention can improve the detection of the growth phase or biological activity for highly resistant microorganisms (e.g., endospores or bacterial spores such as, but not limited to, *Bacillus subtilis, Bacillus atrophaeus*, and *Geobacillus stearothermophilus*) by focusing on volatile organic compounds (VOC) detection and measurement, where specific VOCs are produced and are quickly found in the headspace of a container that includes a biological indicator in a growth medium when a sterilization cycle is or is not successful. After the VOC concentration is measured, by focusing on a change in impedance or resistance when a VOC comes into contact with a film that is part of the biological indicator system, a user interface (UI) can analyze and transmit the growth or biological activity results to end users post sterilization. The time for detecting and reporting of the growth or biological activity can be shortened to less than about 30 minutes, such as less than about 15 minutes, such as less than about 5 minutes. This time frame is much quicker than current methods that require culturing growth medium for turbidity, which can take as long as 2-7 days to verify that a sterilization cycle was successful when there is a lack of turbidity. Further, no fluorescence measurements are required, which can take up to several hours depending on the measurement system and involve additional complications and room for error due to the use of various reagents and enzymes with multiple process steps that must be followed. The biological indicator system may be used in the sterilization of medical devices including full instrument sets, stacked or layered trays, and mixed loads in the current sterilization packaging systems (e.g., sterilization wrap, rigid containers and pouches). Further, the biological indicator system provides for rapid and sensitive microbial VOC detection and also allows for the tracking of the status of the biological indicator being tested, with wireless reporting using RFID technology. Additionally, an RFID reader can detect and received data from multiple RFID tags or an array of RFID tags simultaneously to produce a multiplexed detection system.

Particular VOCs that can be identified by the systems and methods of the present invention based on a measured impedance or resistance level and that are indicative of an unsuccessful sterilization cycle due to the presence of spores in growth medium include ketones, alcohols, esters, and furans. In particular, the VOCs that can be detected in the presence of spores regardless of the type of growth medium utilized can include 2-pentanone, methyl isobutyl ketone, and 4-methyl-2-heptanone in the ketone family; 2-methyl-2-propanol, amylene hydrate, and 2-methyl-1,3-pentanediol in the alcohol family; 3-hydroxy-2,4,4-trimethylpentyl 2-methylpropanoate and 2,2,4-Trimethyl-1,3-pentanediol diisobutyrate in the ester family; and tetrahydro-2,2,5,5-tetramethyl-furan in the furan family. Further, it is to be understood that the systems and methods of the present invention can include an algorithm to subtract out baseline VOC levels that may be emitted by the growth medium and to differentiate between VOCs that may be released by the spores during germination and those that are present in the growth medium alone.

With reference to the figures, the present invention will now be discussed in more detail.

Turning first to FIG. 1, an exploded view of an embodiment of a biological indicator system 100 contemplated by the present invention, including a radiofrequency identification (RFID) sensing board 104, is shown. The RFID sensing board 104 can be disposed between a headspace 146 of a container 108 and a cap 102 for the container 108. The container 108 can include a growth medium 110 containing a biological indicator 112. Further, the headspace 146 can span a distance D between the growth medium 110 and the cap 102 that ranges from about 4 millimeters to about 16 millimeters, such as from about 5 millimeters to about 15 millimeters, such as from about 6 millimeters to about 14 millimeters when the container 108 is sealed. The biological indicator 112 can be any suitable microorganism that exhibits growth in the absence of a successful sterilization cycle, whether the sterilization cycle is dynamic air removal steam (pre-vacuum and gravity), hydrogen-peroxide, or ethylene oxide based. For instance, the microorganisms can be endospores or bacterial spores including, but not limited to, *Bacillus subtilis, Bacillus atrophaeus*, or *Geobacillus stearothermophilus*. Further, the growth medium 110 can be any suitable medium utilized to validate the efficacy of sterilization procedures. For instance, the growth medium can be any growth medium which meets the requirements for growth promoting ability specified in ANSI/AAMI/ISO 11138-1:2006/®/2010. Specific, non-limiting examples include tryptic soy broth and modified soybean casein digest broth.

As shown, the RFID sensing board 104 can be separated from the headspace 146 of the container 108 by a filter 106. The filter 106 can help prevent moisture from the growth medium 110 in the container 108 from coming into contact and possibly damaging the RFID sensing board 104. The filter 106 can include a coating formed from a moisture repellent polymer, such as fluorinated or perfluorinated compounds and ensures that only volatile organic compound (VOC) vapors reach the sensing component of the RFID sensing board 104, as discussed below. The coating can have a thickness ranging from about 0.01 micrometers to about 5 micrometers, such as from about 0.05 micrometers to about 4 micrometers, such as from about 0.1 micrometers to about 3 micrometers. Further, in some embodiments, the filter can be in the form of a film.

Turning now to the specifics of the RFID sensing board 104, as seen in FIGS. 1 through 5, the RFID sensing board 104 can have an upper surface 114 and a lower surface 116. The upper surface 114 can include a radiofrequency identification (RFID) tag 121 that includes an antenna 118 and a radiofrequency integrated circuit (RFIC) 120. The upper surface 114 of the RFID sensing board 104 can also include a microcontroller/digital electronics 122, a signal processing unit 124, a circuit 126, and a temperature sensor 128. Meanwhile, the lower surface 116 can include one or more sensing pads 132 that each include and/or be in contact with a gap electrode 130 for detecting particular VOCs that may be produced by a biological indicator 112 and present in the headspace 146 of the container 108 when a sterilization cycle is not successful. How each of these components facilitate the detect the absence or presence of particular VOCs to determine if a sterilization process was successful or not successful will now be discussed in more detail.

Figure 5:
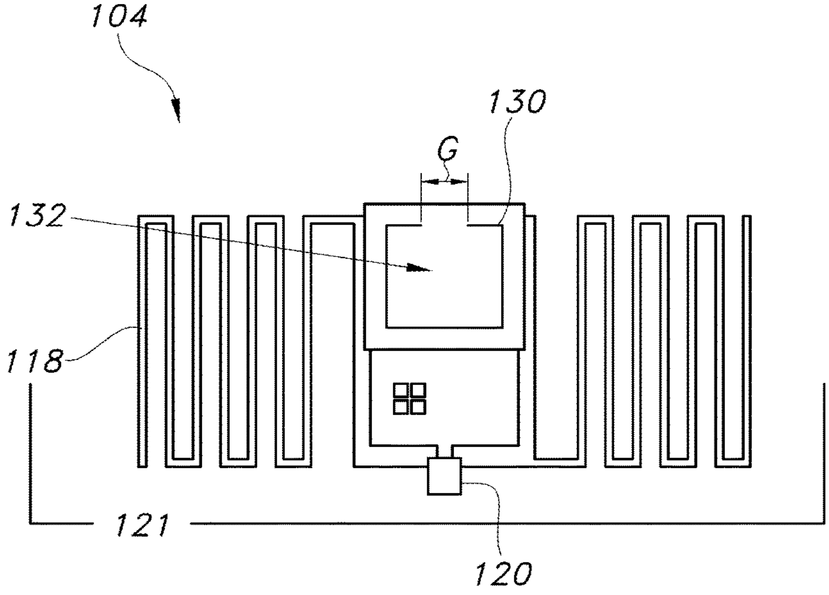
FIG. 5 is a schematic view of a portion of the biological indicator system of FIG. 4.
Figure 6:
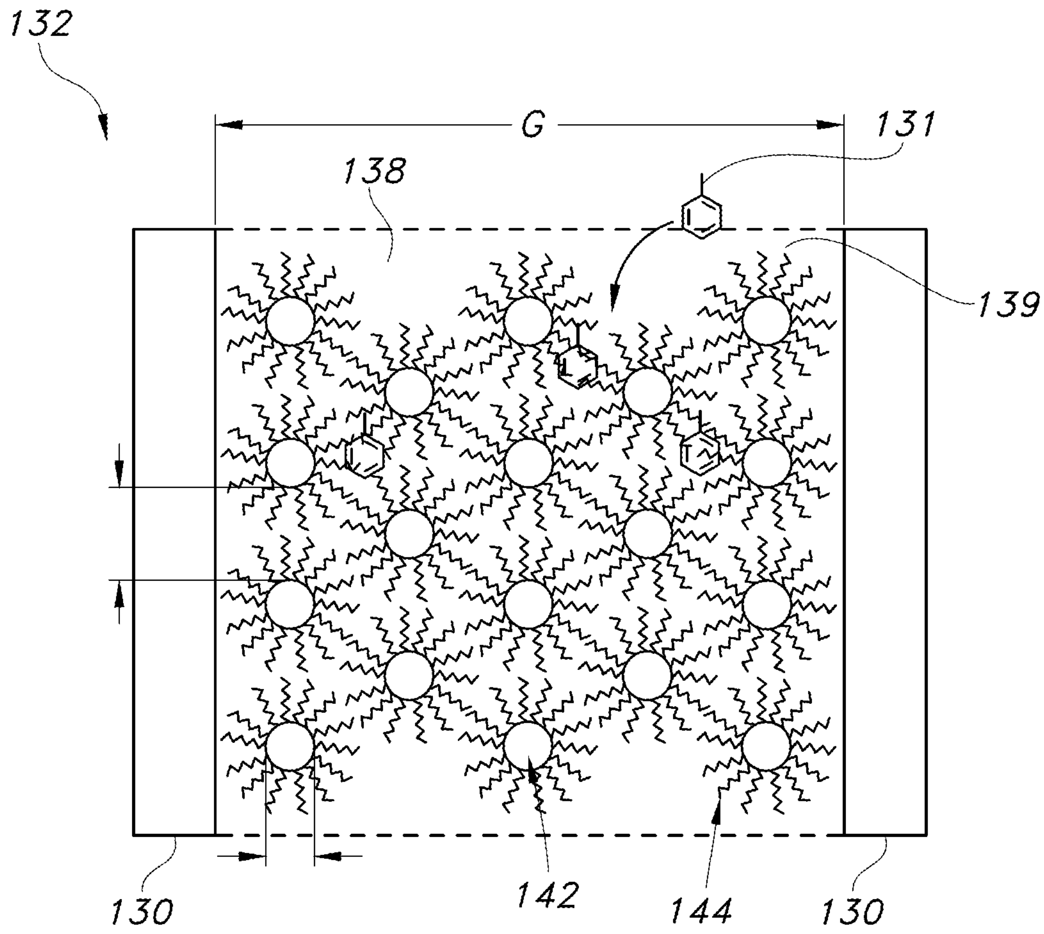
FIG. 6 is a zoomed in view of an embodiment of a sensing pad utilized in a biological indicator system contemplated by the present invention.

First, any VOCs emitted by the biological indicator 112 in the growth medium 110 after sterilization will collect in the headspace 146 of the container 108. The VOC vapor will then pass through the filter 106 to the sensing pad 132 present on the lower surface 116 of the RFID sensing board 104. Referring to FIGS. 5 and 6, the VOCs will contact a film 138 on a gap electrode 130 present on the sensing pads 132. The gap G can range from about 0.01 millimeters to about 0.3 millimeters, such as from about 0.05 millimeters to about 0.25 millimeters, such as from about 0.1 millimeters to about 0.2 millimeters. The film 138 can include metal nanoparticles 142 having a ligand 144 that are embedded in a polymer 139 that forms the film 138. As the VOC of interest 131 contacts the film 138 on each particular sensing pad 132, the film 138 can expand due to the interaction between the VOC and the polymeric film 138, including the nanoparticles 142 and the ligand 144, resulting in an impedance or resistance change in the film 138 that is associated with each particular VOC 131 binding to the nanoparticles 142 via the ligands 144 in order to identify the presence of the VOC 131. Referring to the system 200 shown in FIG. 4, the impedance change or resistance change is measured by the circuit 126. Then, the impedance data or the resistance data is sent through a signal processing unit 124 to a microcontroller 122, which interacts with the RFIC 120. The microcontroller 122 converts the signals received from the circuit 126 from analog to digital, and the signals are then sent to the RFIC 120 of the RFID tag 121, which stores the data. The microcontroller 122 also houses the algorithm to determine accurate impedance and/or resistance measurements.

Further, the antenna 118 is linked to the RFIC 120 and also backscatters a wireless signal 134 that can be detected by an RFID reader 136, which receives the impedance data or resistance data. The antenna 118 can communicate with an RFID reader 136 that can be located up to about 10 meters from the antenna 118, such as about 7.5 meters from the antenna 118, such as about 5 meters from the antenna 118. The RFID reader 136 can then transmit the data to a user interface 148 for further analysis to determine the presence or absence of particular VOCs based on the impedance levels or resistance levels measured. The RFID tag 121 and RFID reader 136 can operate at ultrahigh frequencies (e.g., about 300 Megahertz to about 3 Gigahertz) or high frequencies (e.g., about 3 Megahertz to about 30 Megahertz). Moreover, because the container 108 housing the RFID sensing board 104 will be exposed to temperatures as high as about 120° C. to about 135° C. or greater, it is important to note that the RFID sensing board 104 is free of a battery. Instead, power is provided or harvested from the RFID reader 136.

Additionally, the RFID sensing board 104 also allows for the measurement of the temperature inside the container 108 via the temperature sensor board 128. As with the impedance level data or the resistance level data, the temperature data is received by the microcontroller 122 where it is converted from an analog signal to a digital signal and sent to the RFIC 120. Moreover, it is to be understood that the microcontroller 122 is not limited to storing information associated with impedance, resistance, and temperature and can be used for other sensor readings and data storage. In addition, the microcontroller 122 is configured to measure such values simultaneously.

Moreover, the user interface 148 displays the measured sensor data (e.g., impedance, resistance, temperature, etc.) simultaneously, and the impedance data and/or resistance data displayed can be calibrated based on the type of sterilization cycle that was run (e.g., steam, hydrogen peroxide, ethylene oxide, etc.), as the different types of sterilization cycles may result in the emission of different VOCs, which are associated with different impedance or resistance levels.

Figure 2:
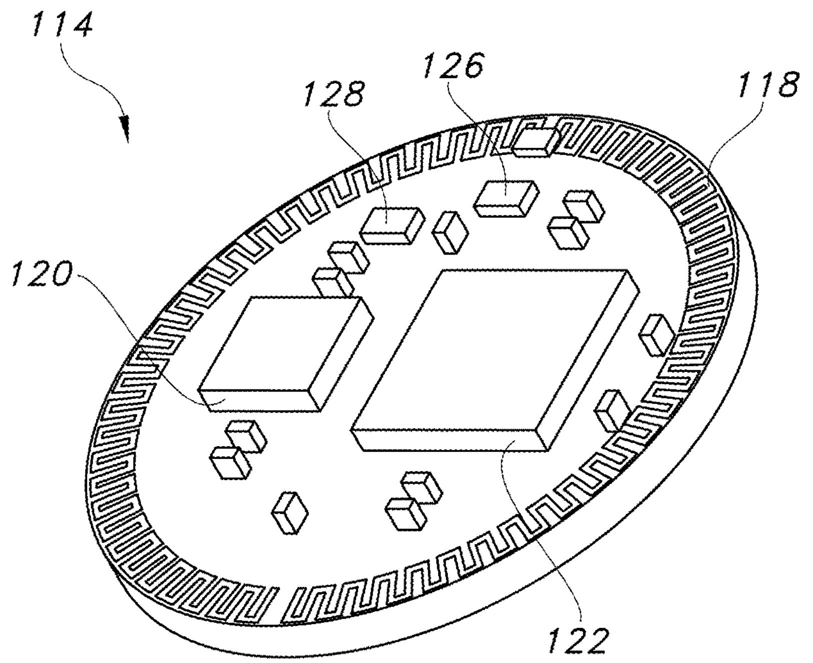
FIG. 2 is a perspective view of an upper surface of the RFID sensing board of FIG. 1.
Figure 3:
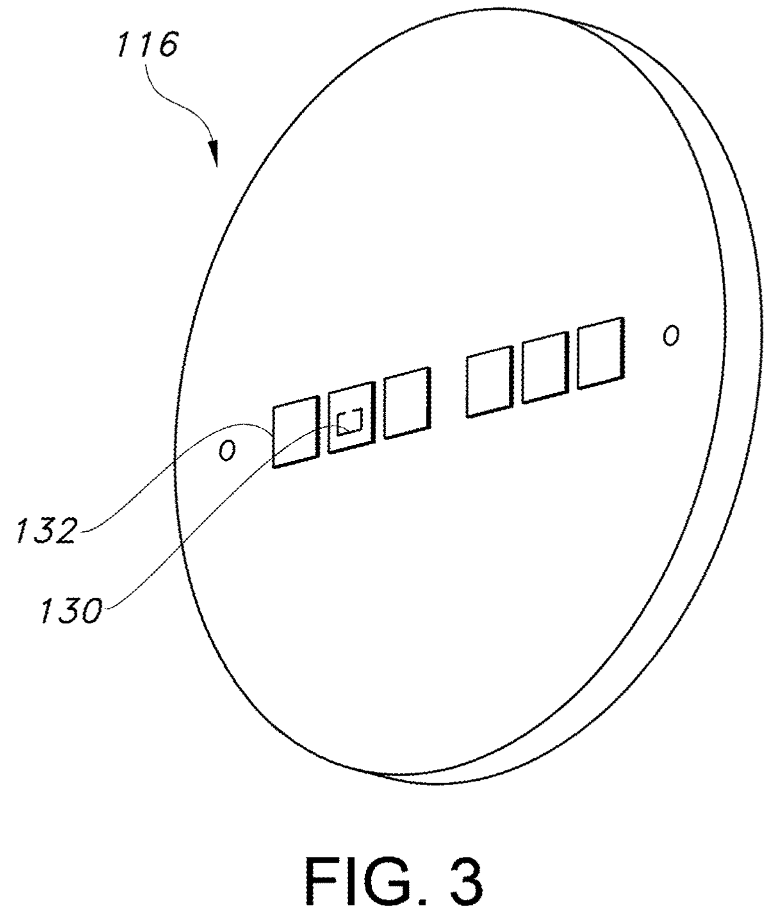
FIG. 3 is a perspective view of a lower surface of the RFID sensing board of FIG. 1.
Figure 4:
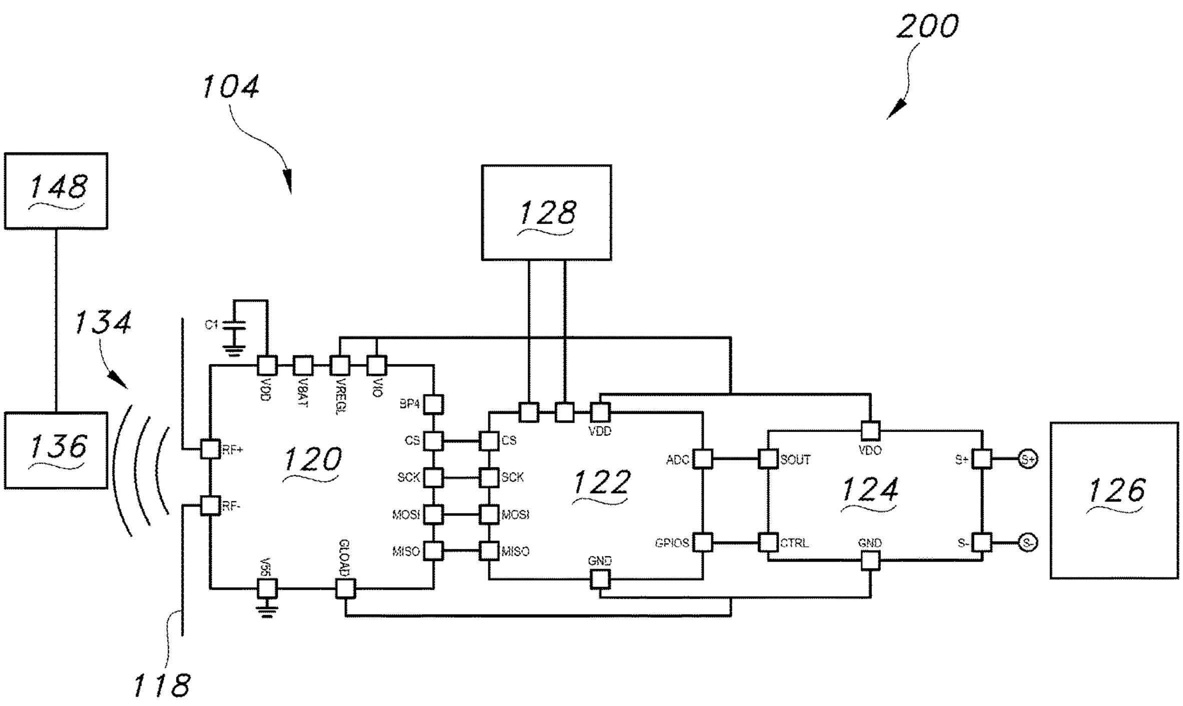
FIG. 4 is a schematic view of an embodiment of a biological indicator system contemplated by the present invention.

As shown in FIG. 5, the RFID tag 121 includes both the antenna 118 and the RFIC 120. As shown in FIG. 2, in order to obtain an adequate signal, the antenna 118 extends around the circumference of the upper surface 114 of the RFID sensing board 104. Further, to maximize its surface area, the antenna 118 can have a circuitous pattern around the circumference of the RFID sensing board 104 as shown. It should be understood that multiple RFID tags 121 can be included on the RFID sensing board 104 in an array in order to receive data from multiple sensing pads 132 regarding the impedance levels and/or resistance levels associated with each sensing pad 132, which can enable the detection and identification of multiple VOCs.

Figure 7:
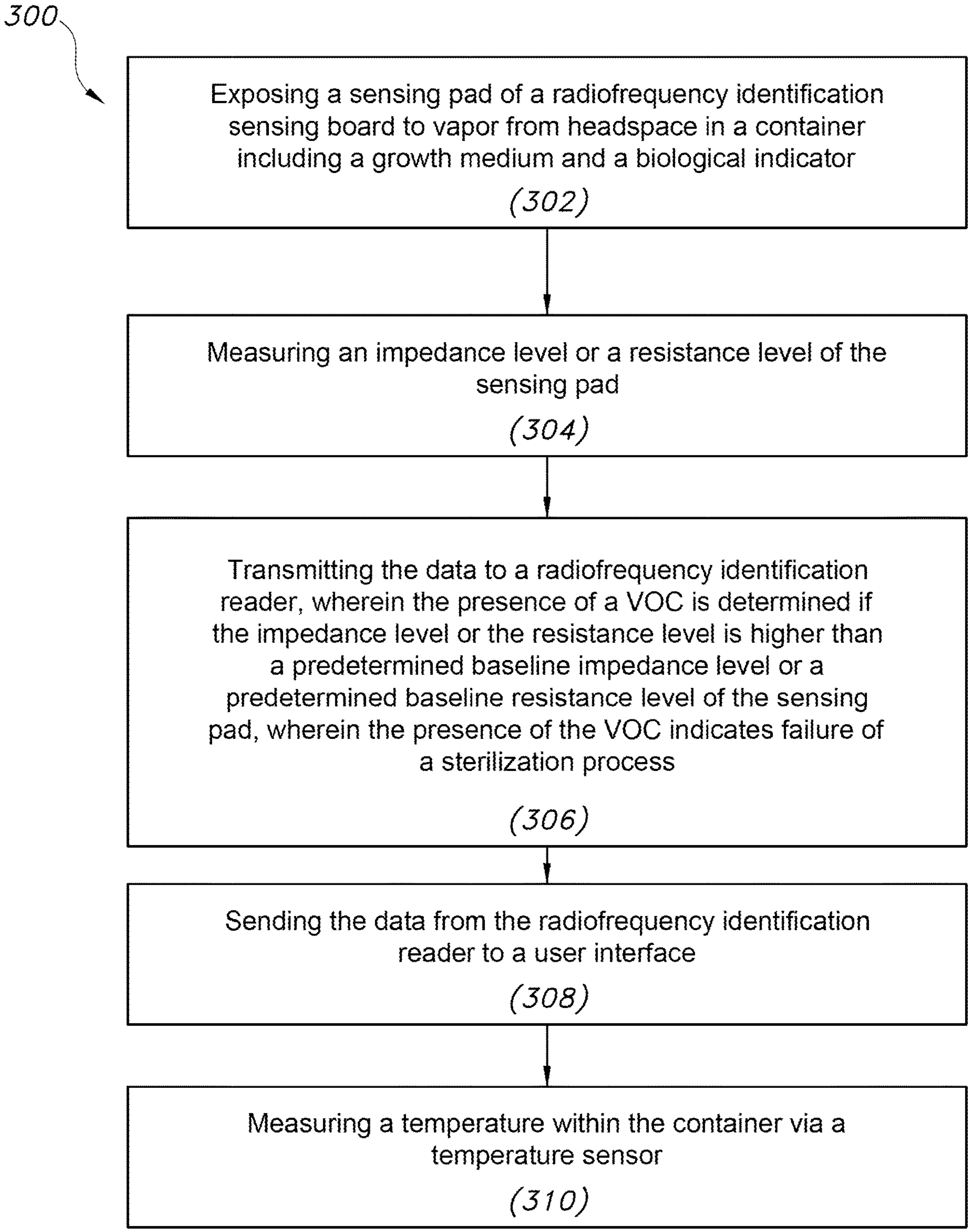
FIG. 7 is a flow chart illustrating a method of using the biological indicator system of the present disclosure to determine the efficacy of a sterilization process.

Turning now to FIG. 7, a flow chart illustrating a method 300 of using the biological indicator system 100, 200 of the present disclosure to determine the efficacy of a sterilization process is shown. After a sterilization process has been completed while the container 108 of the system 100, 200 was present in the sterilization chamber along with the products to be sterilized, the method 300 to verify the efficacy of the sterilization process can include step 302. Step 302 involves exposing a sensing pad of a radiofrequency identification sensing board to vapor from headspace in the container (e.g., an integrated self-contained biological indicator). It should be understood that the integrated SCSI has been exposed to a sterilization process, whether it be steam, hydrogen peroxide, or ethylene oxide based. The method can further include step 304, which involves measuring an impedance level or a resistance level of the sensing pad. Additionally, the method can include step 306, which involves transmitting the data to a radiofrequency identification reader, wherein the presence of a VOC is determined if the impedance level or the resistance level is higher than a predetermined baseline impedance level or a predetermined baseline resistance level of the sensing pad, wherein the presence of the volatile organic compound indicates failure of a sterilization process. The method can also include step 308, which involves sending the data from the radiofrequency identification reader to a user interface. Moreover, the method can include step 310, which involves measuring a temperature within the container via a temperature sensor. Further, the temperature data can be sent to the RFID reader in the same manner as the impedance or resistance data. It should be understood that any of the steps described above can be applied in any suitable order or combined into steps as would be understood by one having ordinary skill in the art.

Figure 8:
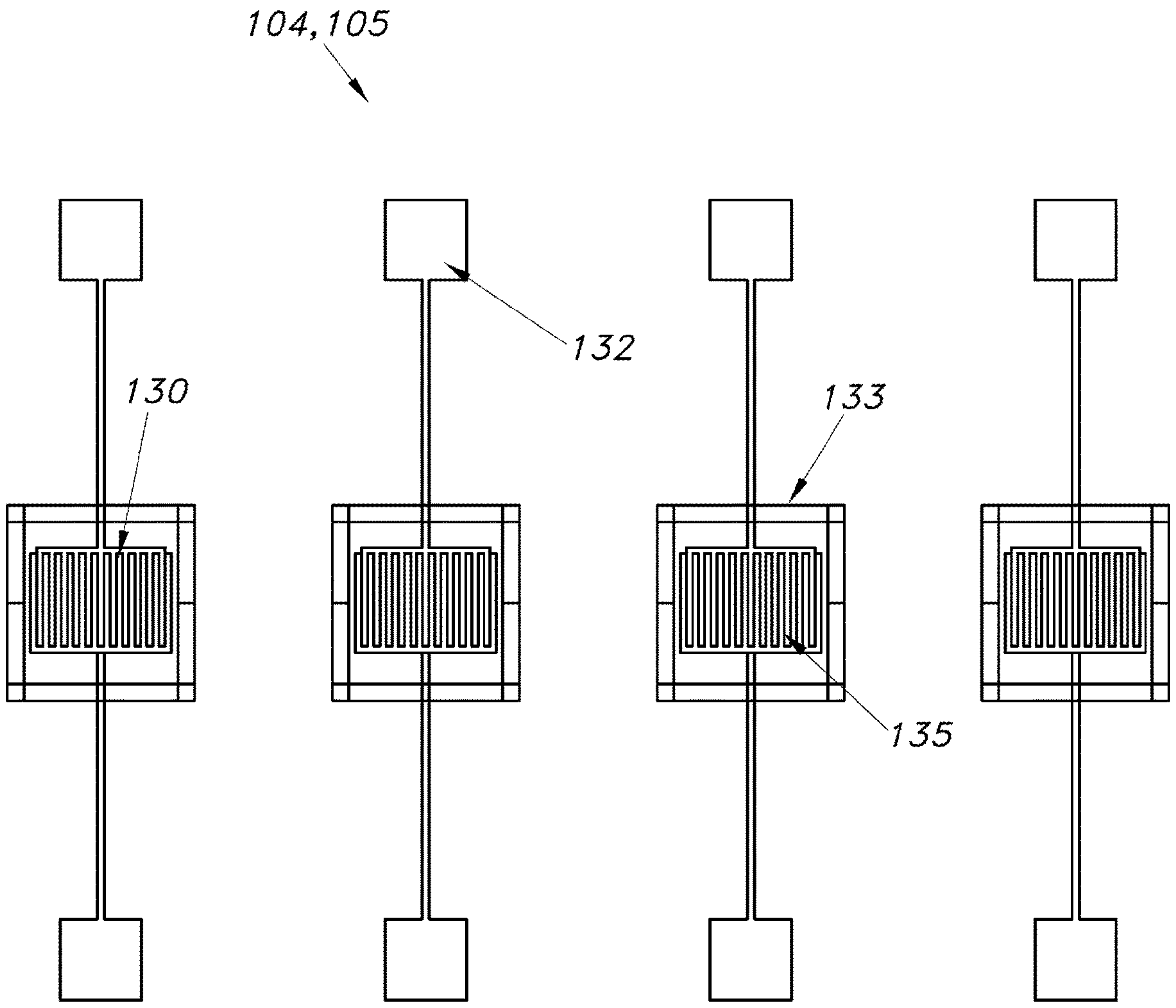
FIG. 8 is a zoomed in view of a portion of another embodiment of an RFID sensing board contemplated by the present invention that utilizes multiple interdigitated electrodes, sensing pads, antennae, and radiofrequency integrated circuits (RFICs) as part of an array of RFID tags to allow for multiplexed measurements.

Meanwhile, FIG. 8 is a zoomed in view of a portion of another embodiment of an RFID sensing board 104 contemplated by the present invention that utilizes multiple interdigitated electrodes 130 and measurement pads or sensing pads 132 to allow for multiplexed measurements. In this example, there are four electrodes 130 shown in the array 105, and the RFID sensing board 104 includes a boundary 133 for ink deposition around the interdigitated electrodes 130 in the array, where it is to be understood that the interdigitated electrodes 130 are coated with a film 138 as described above, and the distance or gap G between adjacent arms or fingers 135 of the interdigitated electrode 130 can range from about 0.01 millimeters to about 0.3 millimeters, such as from about 0.02 millimeters to about 0.25 millimeters, such as from about 0.03 millimeters to about 0.2 millimeters. The average resistance after ink deposition for each interdigitated electrode 130 can range from about 2 Megaohms to about 5 Megaohms, such as from about 2.25 Megaohms to about 4.75 Megaohms, such as from about 2.5 Megaohms to about 4.5 Megaohms.

Figure 9:
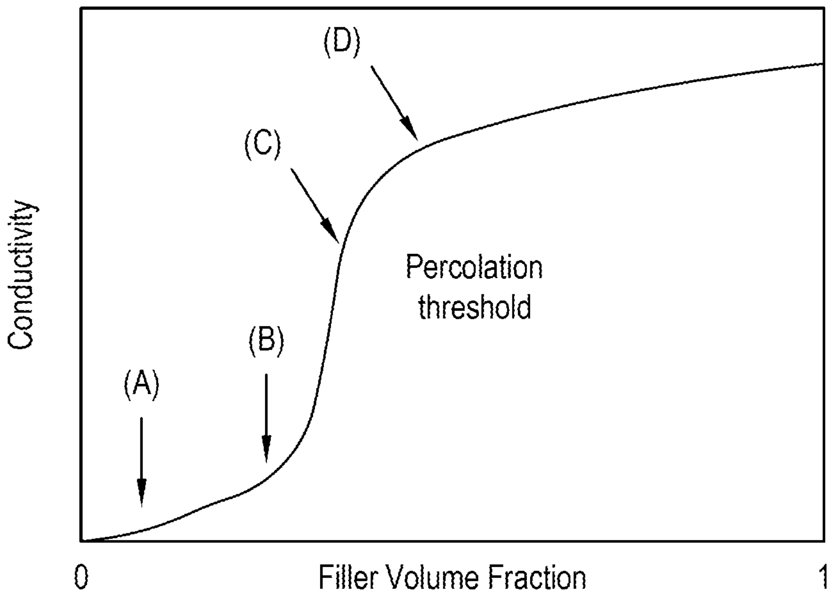
FIG. 9 is a graph illustrating the relationship between nanocomposite conductivity and filler volume fraction of nanoparticles contained within a film.

Next, FIG. 9 is a graph that illustrates the relationship between nanocomposite conductivity and filler volume fraction of nanoparticles 142 contained within a polymer 139 that forms a nanocomposite film 138 that is part of an RFID tag 121 contemplated by the present invention. In particular, in the first stage (A), the conductivity of the nanocomposite film 138 is low as a small number of nanoparticles 142 are isolated inside the polymer 139. The conductivity of the composite material or film 138 is almost the same as that of the polymer 139. In the second stage (B), clusters of nanoparticles 142 are formed with more filler nanoparticles 142 inside the polymer 139. In this state, tunneling occurs between adjacent nanoparticles 142, resulting in a gradual increase in the conductivity of the composite material or film 138. In the third phase (C), a complete electrical path is formed between the nanoparticles 142 as the number of nanoparticles 142 approaches percolation threshold. The conductivity of composite materials or films 138 at this stage increases rapidly. In the final phase (D), as more filler nanoparticles 142 are added to the polymer 139, the conductivity of the composite material or film 138 gradually increases. The most sensitive sensing response for the nanocomposite film 138 is obtained when the nanoparticle volume fraction is between stages (B) and (C).

Figure 10:
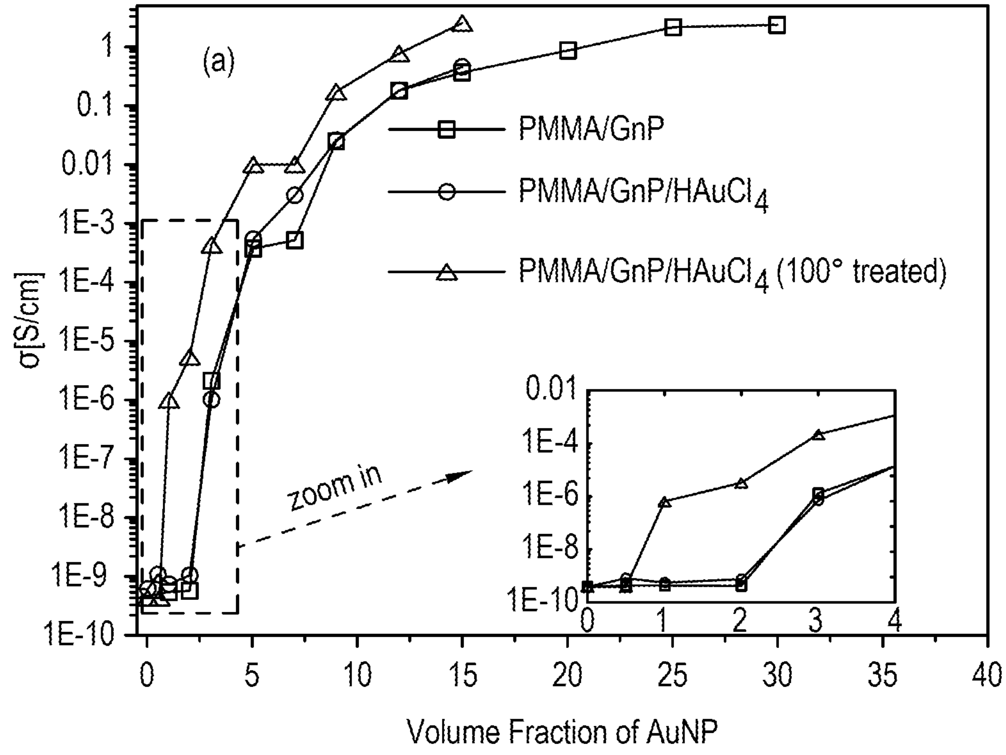
FIG. 10 is a graph illustrating the relationship between conductivity of a nanocomposite containing gold nanoparticles in an acrylate polymer based on the volume fraction of gold nanoparticles present in the film.

FIG. 10 is a graph illustrating the relationship between conductivity of a nanocomposite or film 138 containing gold nanoparticles (GnP) and with and without chloroauric acid ($HauCl_4$) in an acrylate polymer (PMMA) based on the volume fraction of gold nanoparticles present in the film. As known in the art, the conductivity a (S/cm) of a nanocomposite or film is related to the resistance R based on the following formula:

$$R = L/(\sigma A)$$

Where L is the distance or gap G between electrodes and A is the cross-sectional area of the coated nanocomposite film on the electrode. For the present invention, the targeted conductivity for the nanocomposite film should range from about 1E-8 S/cm to about 1E-3 S/cm, which corresponds to a resistance value of from about 100 kiloohms to 1000 about Megaohms. However, due to issues with the accuracy of measuring high resistances (e.g., those above 10 Megaohms) from the leakage current, the targeted resistance of the film of the present invention can range from about 100 kiloohms to about 10 Megaohms.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A biological indicator system for determining the efficacy of a sterilization process, the biological indicator system comprising:

a radiofrequency identification sensing board comprising a radiofrequency identification tag that includes a radiofrequency integrated circuit and an antenna, a microcontroller, a sensing pad, and a circuit coupled to the sensing pad, wherein the radiofrequency identification sensing board is configured to detect an absence or a presence of a volatile organic compound by measuring a change in an impedance level or resistance level of the sensing pad caused by an exposure to the volatile organic compound.

2. The biological indicator system of claim 1, further comprising a biological indicator and a growth medium, wherein the radiofrequency identification sensing board, the biological indicator, and the growth medium are sealed within a container by a cap.

3. The biological indicator system of claim 2, wherein a headspace distance between the growth medium and the cap ranges from about 4 millimeters to about 16 millimeters.

4. The biological indicator system of claim 2, wherein a filter is disposed between the radiofrequency identification sensing board and the growth medium.

5. The biological indicator system of claim 4, wherein the filter includes a polymer coating having a thickness ranging from about 0.01 micrometers to about 5 micrometers.

6. The biological indicator system of claim 1, wherein the sensing pad is disposed on a lower surface of the radiofrequency identification sensing board.

7. The biological indicator system of claim 6, wherein the sensing pad is in contact with a gap electrode or an interdigitated electrode coated with a film.

8. The biological indicator system of claim 7, wherein the gap electrode defines a gap ranging from about 0.01 millimeters to about 0.3 millimeters.

9. The biological indicator system of claim 7, wherein the film comprises a polymer and metal nanoparticles.

10. The biological indicator system of claim 1, further comprising an array of sensing pads.

11. The biological indicator system of claim 1, further comprising an array of radiofrequency indicator tags.

12. The biological indicator system of claim 1, further comprising a radiofrequency identification reader coupled to a user interface.

13. The biological indicator system of claim 12, wherein the radiofrequency identification reader provides power to the radiofrequency identification sensing board.

14. The biological indicator system of claim 12, wherein the radiofrequency tag transmits data to the radiofrequency identification reader at a frequency ranging from about 300 Megahertz to about 3 Gigahertz.

15. The biological indicator system of claim 12, wherein the radiofrequency tag transmits data to the radiofrequency identification reader at a frequency ranging from about 3 Megahertz to about 30 Megahertz.

16. The biological indicator system of claim 1, wherein the radiofrequency identification sensing board is free of a battery.

17. The biological indicator system of claim 1, further comprising a temperature sensor.

18. A method for determining the efficacy of a sterilization process via a biological indicator system comprising a radiofrequency identification sensing board and a radiofrequency identification reader, the method comprising:

exposing a sensing pad of the radiofrequency identification sensing board to a vapor from headspace in a container, wherein the container includes a growth medium and a biological indicator, wherein the radio identification sensing board is configured to detect an absence or a presence of a volatile organic compound in the vapor;

measuring an impedance level or a resistance level of the sensing pad; and sending data associated with the impedance level or the resistance level to a radiofrequency identification tag, wherein the presence of a volatile organic compound is determined if the impedance level or the resistance level is higher than a predetermined baseline impedance level or baseline resistance level of the sensing pad, wherein the presence of the volatile organic compound indicates failure of the sterilization process.

19. The method of claim 18, further comprising transmitting the data to a radiofrequency identification reader.

20. The method of claim 19, further comprising sending the data from the radiofrequency identification reader to a user interface.

21. The method of claim 18, further comprising measuring a temperature within the container via a temperature sensor.

22. The method of claim 18, wherein the radiofrequency identification sensing board comprises a radiofrequency tag that includes a radiofrequency integrated circuit and an antenna, a microcontroller or digital electronics, and an electrical circuit configured to measure the impedance level or the resistance level of the sensing pad.

23. The method of claim 22, further comprising an array of radiofrequency indicator tags.

24. The method of claim 22, wherein the radiofrequency tag transmits data to the radiofrequency identification reader at a frequency ranging from about 300 Megahertz to about 3 Gigahertz.

25. The method of claim 22, wherein the radiofrequency tag transmits data to the radiofrequency identification reader at a frequency ranging from about 3 Megahertz to about 30 Megahertz.

26. The method of claim 18, wherein a cap seals the radiofrequency identification sensing board, the biological indicator, and the growth medium within the container, wherein a headspace distance between the growth medium and the radiofrequency identification sensing board ranges from about 4 millimeters to about 16 millimeters.

27. The method of claim 18, wherein a filter is disposed between the radiofrequency identification sensing board and the growth medium.

28. The method of claim 27, wherein the filter includes a polymer coating having a thickness ranging from about 0.1 micrometers to about 5 micrometers.

29. The method of claim 18, wherein the sensing pad is in contact with a gap electrode or an interdigitated electrode coated with a film comprising a polymer and metal nanoparticles.

30. The method of claim 29, wherein the gap electrode defines a gap ranging from about 0.01 millimeters to about 0.3 millimeters.

31. The method of claim 18, wherein the radiofrequency identification sensing board includes an array of sensing pads.

32. The method of claim 18, wherein the radiofrequency identification reader is coupled to a user interface.

33. The method of claim 18, wherein the radiofrequency identification reader provides power to the radiofrequency identification sensing board.

34. The method of claim 18, wherein the radiofrequency identification sensing board is free of a battery.

35. The method of claim 18, wherein the sterilization process utilizes steam, hydrogen peroxide, or ethylene oxide.

* * * * *